United States Patent [19]

Lafon

[11] Patent Number: 4,490,407
[45] Date of Patent: Dec. 25, 1984

[54] METHOD FOR PREPARING GALENIC FORMULATIONS PARTICULARLY FOR PHARMACEUTICAL, DIETETICAL, COSMETIC AND DIAGNOSTIC USES

[75] Inventor: Louis Lafon, Paris, France

[73] Assignee: Laboratoire L. Lafon, Maisons-Alfort, France

[21] Appl. No.: 482,904

[22] Filed: Apr. 7, 1983

[30] Foreign Application Priority Data

Jan. 25, 1983 [FR] France .................. 83 01115

[51] Int. Cl.$^3$ .................. A01N 1/02; F26B 5/06
[52] U.S. Cl. .................. 427/2; 34/5; 34/13; 264/7; 427/3
[58] Field of Search .................. 264/5, 7; 427/2, 3; 34/5, 13

[56] References Cited

U.S. PATENT DOCUMENTS 4,178,695  12/1979  Erbeia .................. 34/5

FOREIGN PATENT DOCUMENTS 1227744  4/1971  United Kingdom .
1310824  3/1973  United Kingdom .
1328641  8/1973  United Kingdom .

*Primary Examiner*—Michael R. Lusignan
*Attorney, Agent, or Firm*—Young & Thompson

[57] ABSTRACT

A method for preparing a galenic formulation for pharmaceutical, dietetic, cosmetic or diagnostic use, comprising forming a liquid mixture containing at least one active ingredient and at least one film-forming substance, spraying the mixture at a temperature between 50° and 150° C. to form droplets, drying the droplets in a current of drying gas at a temperature between 100° and 150° C. to obtain coated granules with a diameter comprised between 10 and 20$\mu$, collecting the coated granules, and subjecting the collected granules to lyophilization.

5 Claims, No Drawings

METHOD FOR PREPARING GALENIC FORMULATIONS PARTICULARLY FOR PHARMACEUTICAL, DIETETICAL, COSMETIC AND DIAGNOSTIC USES

The present invention relates to a new method for preparing galenic formulations particularly for pharmaceutical, dietetic, cosmetic and diagnostic uses. It also relates, as new industrial products, to the galenic formulations obtained according to said process which includes a projection- or spray-drying and lyophilization.

It is known from U.S. Pat. No. 4,178,695 to prepare pharmaceutical, cosmetic and diagnostic formulations by lyophilization of at least one active ingredient in solution or in suspension in a solvent or solvent mixture, wherein the solution or suspension is locally and progressively cooled in controlled manner, under stirring, so as to cause the production of microcrystals of solvent which are placed in suspension in the remainder of the liquid until a high-viscosity microcrystalline complex system is obtained which is essentially composed of isolated microcrystalline crystals of solvent intimately mixed with interstitial liquid phases having a high concentration of the initially present substances, and wherein the microcrystalline complex system is hardened by cooling and lyophilized.

It is also known, according to said patent, that it is possible to add to the mass of microcrystalline complex system, solid products such as coated or encapsulated granules.

It has also been proposed, in British Pat. Nos. 1,227,744, 1,310,824 and 1,328,641, to use processes for preparing pharmaceutical, cosmetic and diagnostic formulations which comprise the lyophilization of at least one active ingredient in solution or in suspension in water or in an organic solvent or else in an oil-in-water type emulsion, in combination with an excipient which, in some cases, can contain colloids, and polysaccharides (such as gum arabic, alginates, pectinates, polyethyleneglycols, carboxymethylcellulose and polyvinylpyrrolidone, for example), a soluble and edible stabilizing agent (such as lactose, glucose, saccharose, mannitol and glycocoll) and/or substances permitting obtaining an effervescent effect, such as for example $CO_2$-producing effervescent mixtures, constituted by an organic acid such as citric acid, tartric acid, ascorbic acid, and a slightly mineral base such as alkali and alkaline-earth carbonates and bicarbonates.

The present invention proposes a new process for obtaining a galenic formulation for dietetic, cosmetic and diagnostic uses, which process consists in:

(1) spraying in droplets form a mixture containing at least one active ingredient and at least one film-forming substance at a temperature of between 50° and 150° C. and drying the formed droplets by means of a current of drying gas introduced at a temperature comprised between 100° and 150° C. according to a mode selected from the group consisting of (i) co-current with respect to the droplets, (ii) counter-current with respect to the droplets, and (iii) co-current and counter-current with respect to the droplets, to obtain coated granules with a diameter comprised between 10 and 120$\mu$; and (2) collecting the particles thus coated and subjecting them to lyophilization.

This process is particularly advantageous for producing gastroresistant galenic formulations which should release the active principle at the level of the intestine.

Amongst suitable film-forming substances, the following polymers can be used: ethylcellulose, cellulose acetophthalate, polyvinylacetate-diethylaminoacetate, the copolymers of 2-methyl-5-vinylpyridine with methacrylic acid and methacrylates and the polymers and copolymers of dimethylaminoethyl methacrylate said polymers being in solution in suitable solvents such as, dichloromethane, chloroform, trichloroethylene, methanol, ethanol and isopropanol. Said solvents are eliminated without any difficulty during the spraying-coating stage.

The best mode consists in using for the spraying a film-forming substance selected from the following: (i) glycerides and polyglycerides of fatty acids such as the mono-glycerol and distearate, and glycerol palmitostearate (ii) polyethyleneglycol, (iii) polyoxyethylene copolymers and polyoxypropylene copolymers, (iv) urea and urethane, and (v) mixtures thereof.

The advantage of these substances is to give at temperatures comprised between 50° and about 100° C., compositions with active ingredients which are known as solid solutions or gels, in which the solid active ingredients are contained in a molten mass.

To lower the treatment temperature, an alcohol such as limonene, cineol, menthol, eugenol or vanillin is incorporated in the mixture of said substances and active principles.

The invention will be more readily understood on reading the following examples of preparation, given non-restrictively by way of illustration.

(A) Solid solutions produced by fusion 1.1 buflomedil: 1 part
  glycerides and polyglycerides of fatty acid: 3 parts
  solution obtained at 50° C.
1.2 buflomedil: 1 part
  mono/distearate of glycerol: 2 parts
  solution obtained at 80° C.
1.3 buflomedil: 1 part
  palmitosterate of glycerol: 3 parts
  solution obtained at 80° C.
1.4 tiadenol: 1 part
  distearate of glycerol: 2 parts
  solution obtained at 80° C.
1.5 spironolactone: 1 part
  polyethylene glycol 6000: 9 parts
  solution obtained at 130°/140° C.
1.6 spironolactone: 1 part
  copolymer of polyoxyethylene and of polyoxypropylene: 9 parts
  solution obtained at 130°/140° C.
1.7 spironolactone: 1 part
  urea: 2 parts
  solution obtained at 135° C.
1.8 spironolactone: 1 part
  urethane: 2 parts
  solution obtained at 60° C.
1.9 indometacine: 1 part
  polyethylene glycol: 9 parts
1.10 acetate of DL$\alpha$ tocopherol 100 mg: 1 part
  polyethylene glycol: 3 parts These different solutions, which are liquid under heat, can be poured directly into unit alveolar packs, or dispersed in fine solid particles by the spray cooling method.

The large surface offered by these last particles is a factor of improvement of the bioavailability of the active principle which they contain; a characteristic which is not found in the molten form, and which can be preserved in a "lyoc" type form obtained according to the aforementioned patents.

(B) Solid solutions obtained by gelling an intermediate solvent

| 2.1 | indometacine | 50 mg |
|---|---|---|
| | N methyl pyrrolidone | 300 mg |
| | polyethylene | 125 mg |
| | polyethylene glycol | 200 mg |

The polyethylene, polyethyleneglycol and indometacine are dissolved under heat in N-methyl-pyrrolidone.

| 2.2. | indometacine | 50 mg |
|---|---|---|
| | polyethylene glycol | 200 mg |
| | limonene | 300 mg |
| | mono/distearate of glycerol | 200 mg |
| 2.3. | spironolactone | 50 mg |
| | distearate of saccharose | 200 mg |
| | limonene | 300 mg |
| | polyethylene glycol | 100 mg |
| 2.4 | spironolactone | 50 mg |
| | polyoxyethylene and polyoxy-propylene copolymer | 200 mg |
| | cineol | 200 mg |

As the foregoing examples demonstrate, it is possible to associate, in these mixtures, the active principle with amphiphilic products or with hydrophobic products in order to modulate their releasing speed.

In all cases, the solutions obtained under heat can be: either poured directly into alveoli corresponding to the unit doses,
or solidified by spray cooling. The fine particles obtained in this way are thereafter incorporated in a "lyoc" formulation such as described in the aforecited patents,
or compacted (the compacting being carried out under low pressure, and the punches being adapted to the required shape and dimensions).

(C) Solid solutions obtained by solidification of a micellar solution or of an emulsion The active ingredient may be dissolved in the aqueous continuous phase or in the dispersed phase.

Solidification is achieved by incorporating a gelling agent in one or the other phase, or in both phases; for example:
gelatin is used as gelling agent for the aqueous phase, cetyl alcohol, stearates and other fatty esters of glycerol can be used as gelling agent for the dispersed anhydrous phase.

Emulsion of the dispersed phase is achieved by means of different surface-active agents.

Solidification of these emulsions, microemulsions or micellar solutions can be achieved:
(1) either by spontaneous cooling and pouring into unit alveoli,
(2) or by spray-drying,
(3) or by spray-cooling.

The particles obtained by this last method can be directly incorporated in a "lyoc" sherbet:

EXAMPLE

| 3.1. | pluronic F 68 (POLOXAMERE 188-DC 1) | 50 mg | |
|---|---|---|---|
| | water | 700 mg | } I |
| | gelatin | 50 mg | |
| | polysorbate 80 | 500 mg | |
| | limonene | 150 mg | |
| | N—methylpyrrolidone | 150 mg | } II |
| | glycerol distearate | 50 mg | |
| | spironolactone | 50 mg | |

Phases I and II are prepared separately at a temperature of about 70°; they are emulsified by mixing at that same temperature.

| 3.2. | Indometacine | 100 mg | } I |
|---|---|---|---|
| | limonene | 200 mg | |
| | glycerol | 100 mg | |
| | gelatin | 50 mg | |
| | water | 500 mg | |
| | lecithine | 25 mg | |
| | glycerol monostearate | 5 mg | |

Phases I and II are heated to 60° and emulsified at that same temperature.

It will thus be seen that the present invention provides a method for preparing a galenic formulation for pharmaceutical, dietetic, cosmetic or diagnostic use, comprising forming a liquid mixture containing at least one active ingredient and at least one film-forming substance, spraying said mixture at a temperature between 50° and 150° C. to form droplets, drying said droplets in a current of drying gas at a temperature between 100° and 150° C. to obtain coated granules with a diameter comprised between 10 and 120μ, collecting said coated granules, and subjecting said collected granules to lyophilization.

What is claimed is:

1. A method for preparing a galenic formulation for pharmaceutical, dietetic, cosmetic or diagnostic use, comprising forming a liquid mixture containing at least one active ingredient and at least one film-forming substance, spraying said mixture at a temperature between 50° and 150° C. to form droplets, drying said droplets in a current of drying gas at a temperature between 100° and 150° C. to obtain coated granules with a diameter comprised between 10 and 120μ, collecting said coated granules, and subjecting said collected granules to lyophilization.

2. A method according to claim 1, wherein the film-forming substance is selected from the group consisting of: ethylcellulose, cellulose acetophthalate, polyvinylacetate-diethylaminoacetate, copolymers of 2-methyl-5-vinylpyridine, methacrylic acid, methacrylates and the polymers or copolymers of dimethylaminoethyl methacrylate.

3. A method according to claim 1, wherein the film-forming substance is selected from the group consisting of
(i) glycerides and polyglycerides of fatty acids,
(ii) polyethyleneglycol,
(iii) polyoxyethylene copolymers and polyoxypropylene copolymers,
(iv) urea and urethane, and
(v) a mixture thereof.

4. A method according to claim 3 wherein the glycerides are selected from the group consisting of glycerol monostearate, glycerol distearate and glycerol palmitostearate.

5. A method according to claim 1, wherein the mixture of film-forming substances with at least one active ingredient comprises at least an alcohol selected from the group consisting of limonene, cineol, menthol, eugenol and vanillin.

* * * * *